United States Patent
Lee et al.

(10) Patent No.: US 10,576,170 B2
(45) Date of Patent: Mar. 3, 2020

(54) GAS-GENERATING NANOPARTICLE

(71) Applicant: INDUSTRY-UNIVERSITY COOPERATION FOUNDATION, HANYANG UNIVERSITY, Seoul (KR)

(72) Inventors: Kuen Yong Lee, Seoul (KR); Jang Wook Lee, Uijeongbu-si (KR)

(73) Assignee: supernova bio Co., Ltd, Seoul (KR)

( * ) Notice: Subject to any disclaimer, the term of this patent is extended or adjusted under 35 U.S.C. 154(b) by 256 days.

(21) Appl. No.: 14/738,003

(22) Filed: Jun. 12, 2015

(65) Prior Publication Data

US 2015/0359751 A1    Dec. 17, 2015

(30) Foreign Application Priority Data

Jun. 13, 2014  (KR) ........................ 10-2014-0072166

(51) Int. Cl.
*A61K 9/14* (2006.01)
*A61K 49/22* (2006.01)

(52) U.S. Cl.
CPC .......... *A61K 49/221* (2013.01); *A61K 49/225* (2013.01)

(58) Field of Classification Search
CPC ...... A61K 49/00; A61K 38/00; A61K 49/221; A61K 47/00; A61K 47/48915; A61K 47/48246; A61K 49/225; A61K 49/004; A61K 49/22; A61K 49/226; A61K 49/222; A61K 49/0093
USPC ...... 424/1.11, 1.65, 1.69, 1.73, 9.1, 9.2, 9.3, 424/9.4, 9.5, 9.6, 1.29, 400, 450, 489, 424/490, 491; 514/1, 1.1, 21.3; 530/300, 530/324; 977/773
See application file for complete search history.

(56) References Cited

U.S. PATENT DOCUMENTS

| | | | | |
|---|---|---|---|---|
| 4,244,933 A | * | 1/1981 | Shibazaki | ............... C01F 11/18 106/409 |
| 7,157,100 B2 | * | 1/2007 | Doshi | .................. A61K 9/0065 424/465 |
| 9,080,014 B2 | * | 7/2015 | Gu | ........................ A61K 9/5153 |

OTHER PUBLICATIONS

Lee, Jangwook, Thesis: "Development of Functionalized Polymeric Nanoparticles for Cancer Diagnosis and Therapy," Department of Bioengineering, The Graduate School, Hanyang University, Aug. 8, 2013.
Krell et al., "Processing of high-density submicrometer $Al_2O_3$ for new applications," J Am Ceram Soc. 86(4):546-53 (2003).
Krell et al., "The influence of shaping method on the grain size dependence of strength in dense submicrometre alumina," Journal of the European Ceramic Society. 16(11):1189-200 (1996).
Luan et al., "Fabrication and characteristics of fine-grained BaTiO3 ceramics by spark plasma sintering," Ceramics International. 30(3): 405-10 (2004).
Oustadakis et al., "Hydrometallurgical process for zinc recovery from electric arc furnace dust (EAFD): Part I: characterization and leaching by diluted sulphuric acid," Journal of Hazardous Materials. 179(1-3):1-7 (2010).
Randall et al., "Intrinsic and extrinsic size effects in fine-grained morphotropic-phase-boundary lead zirconate titanate ceramics," J Am Ceram Soc. 81(3):677-88 (1998).
Takeuchi et al., "Preparation of fine-grained BaTiO3 ceramics by spark plasma sintering," Journal of Materials Research. 17(3):575-81 (2002) (Abstract Only) (4 pages).
Valiev et al., "Direction of a grain-boundary phase in submicrometre-grained iron," Philosophical Magazine Letters. 62(4):253-6 (1990) (Abstract Only) (2 pages).
Zhan et al., "Superplastic behavior of fine-grained beta-silicon nitride material under compression," J Am Ceram Soc. 83(4):841-7 (2000).

\* cited by examiner

*Primary Examiner* — D. L. Jones
(74) *Attorney, Agent, or Firm* — Clark & Elbing LLP; Susan M. Michaud

(57) ABSTRACT

Disclosed are gas-generating nanoparticles comprising fine-grained calcium carbonate crystals and a biocompatible polymer, the fine-grained calcium carbonate crystals being encapsulated inside the biocompatible polymer, and the diagnosis and treatment of diseases can be effectively performed at the same time by using a composition of the present disclosure.

12 Claims, 13 Drawing Sheets

Specification includes a Sequence Listing.

SEQUENCE LISTING

```
<160> NUMBER OF SEQ ID NOS: 1

<210> SEQ ID NO 1
<211> LENGTH: 29
<212> TYPE: PRT
<213> ORGANISM: Rabies virus

<400> SEQUENCE: 1

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25
```

GAS-GENERATING NANOPARTICLE

CROSS-REFERENCE TO RELATED APPLICATION AND CLAIM OF PRIORITY

The present invention was made with the support of the Ministry of Education of the Republic of Korea, under Project No. NRF-2013R1A2A2A03010055, which was conducted in the research project titled "Basic Research project by National Research of Foundation of Korea, project for supporting a Mid-Career researcher", within the project named "Tissue Regeneration Using a Magnetic Field-Sensitive Microgel" by the Industry-Academic Cooperation Foundation, Hanyang University under the management of the National Research of Foundation of Korea, from Jun. 1, 2013 to May 30, 2016.

This patent application claims priority Korean Patent Application Nos. 10-2014-0072166 filed Jun. 13, 2014, in the Korean Intellectual Property Office, the disclosures of which are incorporated in their entirety by reference.

BACKGROUND

Field of the Invention

The present invention relates to gas-generating nanoparticles containing fine-grained calcium carbonate (FCC) crystals and a biocompatible polymer.

Background of Technique

Many contrast agents have been widely developed and used for clinical practice such as X-ray, Ultrasound, MR, CT, and PET [Journal of Clinical Oncology 2008; 26(24): 4012-4021, European Journal of Nuclear Medicine 2000; 27(6):619-627, Expert Opinion on Drug Metabolism & Toxicology 2009; 5(4):403-416]. Toxicity of the agents including renal-toxicities, nausea, hair loss, renal disorder, nephropathy, and nephrogenic systemic fibrosis, has limited their use in clinical cases [Clinical Journal of the American Society of Nephrology 2007; 2(2):264-267, Investigative Radiology 2008; 43(2):141-144]. Although various contrast agents can be improved by polymeric coating and target-ligand conjugation, the potential toxicity still remains and must be resolved.

Recently, non-toxic carbon dioxide gas have attracted considerable attention as a contrast agent [European Journal of Radiology 2006; 60(3):324-330, Pharmaceutical Research 2010; 27(1):1-16, Artificial Cells, Blood Substitutes and Biotechnology 1988; 16(1-3):411-420].

Ultrasound imaging is obtained by acoustic signal based on backscattering or reflection of sound above 20 KHz, and utilized for estimation of organs anatomically and functionally in the body [Heart 1997; 77(5):397-403, European Radiology 2001; 11(8):1316-1328, Ultrasonic Imaging 1979; 1(3):265-279]. The imaging technique has attractive properties such as no insertion or surgery, simplicity, real-time imaging, and low cost as diagnosis tools [Current Opinion in Pulmonary Medicine 2003; 9(4):282-290]. Microbubbles have been applied to ultrasound imaging as contrast agents, however it is inherently unstable and have large sizes during blood circulation [Journal of Biomaterials Science, Polymer Edition 2011; 22(4-6):417-428]. In addition, microbubbles are difficult to functionalize with bioactive molecules.

In the case of classic anti-cancer drugs such as chemical agents and genes, they have confronted with severe side effects due to drug effects on normal tissues [New England Journal of Medicine 2003; 348(6):538-549]. Cancer cells also tend to show drug resistance, leading to vicious cycle of repetitive treatments with high dosage because of reduced effect of subsequent therapy [Annual Review of Medicine 2002; 53(1):615-627]. It is well-known that the cell live and death are controlled by apoptotic and/or necrotic cell death pathways [Cell death and differentiation 1995; 2(2):87-96, Current Opinion in Cell Biology 2004; 16(6):663-669, Oncogene 2004; 23(16):2757-2765]. Meanwhile, cancer therapy focused on the drugs were concerned with not necrotic-cell death pathways but apoptotic the pathways. Necrosis has been considered as accidental and unregulated cell death signaling, but it could be induced by ischemia condition, microbial infection, neuronal excitotoxins, or reactive oxygen species were reported [The Journal of Experimental Medicine 1998; 188(5):919-930, Cell Death and Differentiation 2003; 10(1):45-65].

Despite the various anticancer drugs associated with the cancer cell apoptosis pathway have been consistently developed, they have a technical limitation from complexity of their apoptotic process or acquisition of drug resistance by changing their micro environment. Furthermore, a anticancer drug treatments are considered a secondary treatment because nonspecific anticancer drugs may be accumulated on normal cells and adversely affect the cells.

SUMMARY

The present inventors have endeavored to develop a novel form of composition for diagnosis and treatment, capable of simultaneously diagnosing and treating diseases while solving the problems of the prior art in that the disease-specific diagnosis is difficult due to a short in vivo circulation time and low permeability into the blood of the existing gas form of contrast agent. As a result, the present inventors have established that effective diagnosis and treatment of diseases can be simultaneously attained by using gas-generating nanoparticles composed of fine-grained calcium carbonate crystals and a biocompatible polymer, and have thus completed the present invention.

Accordingly, an aspect of the present invention is to provide gas-generating nanoparticles.

Another aspect of the present invention is to provide a composition for ultrasound imaging, containing the foregoing gas-generating nanoparticles.

Still another aspect of the present invention is to provide a composition for cell necrosis induction using cell bursting due to the instantaneous eruption of condensed gas.

Still another aspect of the present invention is to provide a composition for drug delivery.

Still another aspect of the present invention is to provide a method for preparing the forgoing gas-generating nanoparticles.

Other purposes and advantages of the present disclosure will become more obvious with the following detailed description of the invention, claims, and drawings.

DETAILED DESCRIPTION

Figure 1:
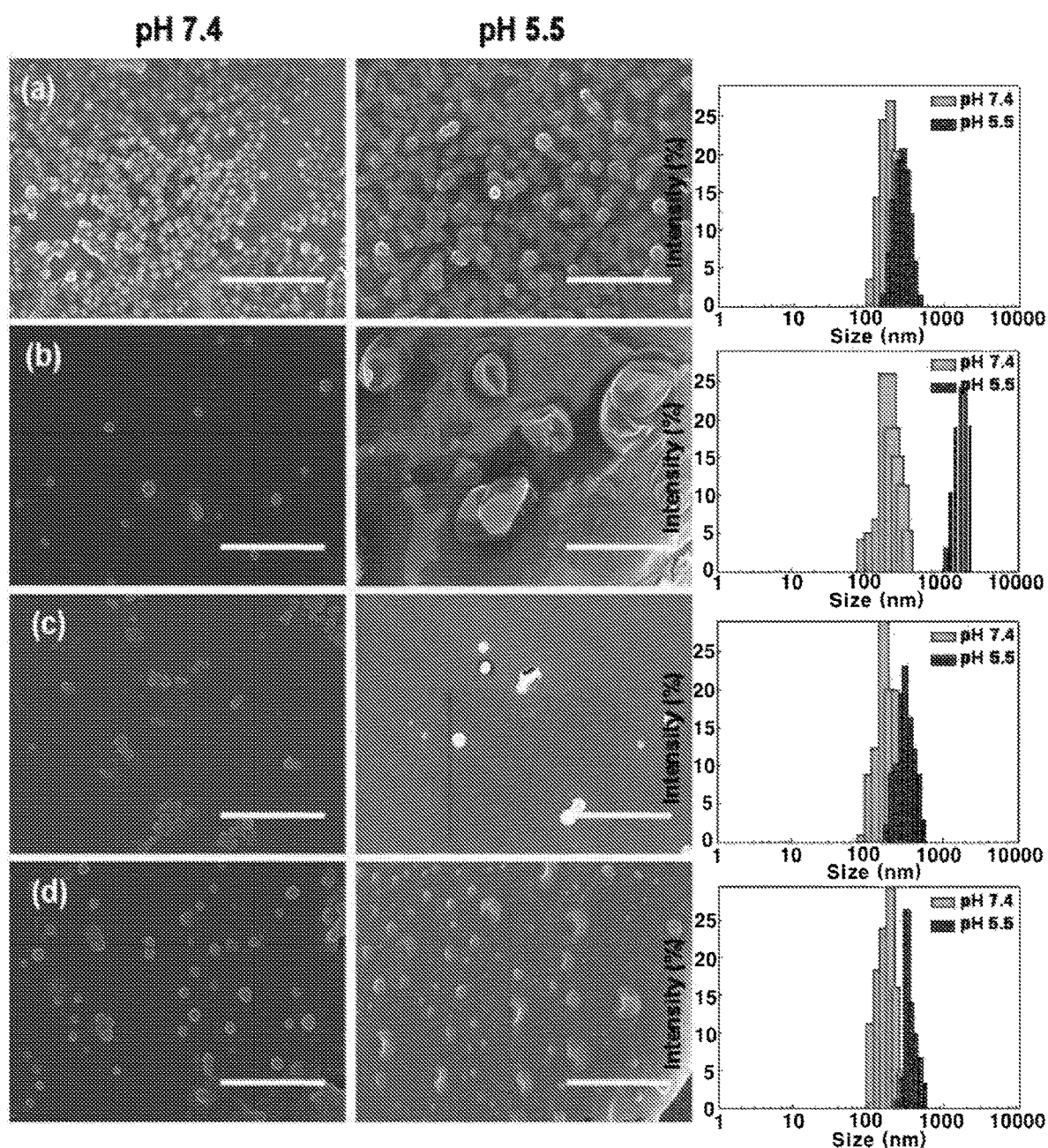
FIG. 1 shows morphology and size distribution of gas-generating PLGA nanoparticles prepared with different calcium carbonate contents ((a) 0, (b) 0.01, (c) 0.1, and (d) 1; $CaCO_3$/PLGA (w/w)). The suspension of nanoparticles in neutral (pH 7.4) and acidic (pH 5.5) buffers was observed by scanning electron microscopy (scale bar=1 μm).

According to an aspect of the present invention, the present invention provides gas-generating nanoparticles including fine-grained calcium carbonate crystals and a biocompatible polymer, the fine-grained calcium carbonate crystals being encapsulated inside the biocompatible polymer.

The present inventors have endeavored to develop a novel form of composition for diagnosis and treatment, capable of simultaneously diagnosing and treating diseases while solving the problems of the prior art in that disease-specific diagnosis is difficult due to a short in vivo circulation time and low permeability into the blood of the existing gas form of contrast agent. As a result, the present inventors have established that the effective diagnosis and treatment of diseases can be simultaneously performed by using gas-generating nanoparticles including fine-grained calcium carbonate crystals and a biocompatible polymer.

As used herein, the term "fine-grained calcium carbonate (FCC) crystals" refers to ones that are differentiated from precipitated calcium carbonate prepared through chemical processing and generally produced by mechanically pulverizing and classifying high-purity crystalline limestone.

The gas-generating nanoparticles of the present invention have a form in which fine-grained calcium carbonate crystals are encapsulated inside a biocompatible polymer, and here, the fine-grained calcium carbonate crystals are stuck without floating inside a hard-shell type spherical structure formed of the biocompatible polymer, which means a solid colloidal structure in which the fine-grained calcium carbonate crystals are uniformly stuck from the core of the spherical structure to the external surface without a significant difference on the distribution probability.

The gas-generating nanoparticles of the present invention cause a reaction in which the fine-grained calcium carbonate encapsulated inside the particles produce carbon dioxide gas at the acidic condition. The gas-generating nanoparticles of the present invention are in a form in which fine-grained calcium carbonate crystals are stuck inside the stuffed solid crystal, but not a core-shell form in which calcium carbonate is contained inside a layered membrane structure. That is, differently from a structure in which the gas generated from the inside leaks to the outside simultaneously with the generation thereof, the fine-grained calcium carbonate crystals contained in the gas-generating nanoparticles produce carbon dioxide gas, gently increasing the internal pressure of the gas-generating nanoparticles, thereby finally inducing the eruption of nanoparticles. These characteristics simultaneously lead to an imaging contrast effect through carbon dioxide gas droplets and a cell bursting effect due to the release of the gas droplets and the eruption of nanoparticles.

In one embodiment of the present invention, the biocompatible polymer of the present invention is surface-modified with the rabies virus glycoprotein (RVG) peptide. The RVG peptide of the present invention may include a rabies virus glycoprotein peptide, or a variant, polypeptide fragment, or derivative thereof. The RVG peptide of the present invention has neuroblastoma-specific targeting. Therefore, the gas-generating nanoparticles surface-modified with the RVG peptide are selectively accumulated in the neuroblastoma tissue, producing carbon dioxide gas in the tissue at the acidic condition in the cancer tissue, thereby allowing cancer-specific ultrasound imaging. Furthermore, the carbon dioxide gas generated from the gas-generating nanoparticles in cancer cells are condensed inside the gas-generating nanoparticles, thereby ultimately deforming and rupturing the structure of the nanoparticles to instantaneously erupt, causing physical bursting of the cells, leading to cell necrosis.

In one embodiment of the present invention, the RVG peptide of the present invention includes an amino acid sequence of SEQ ID NO: 1.

The biocompatible polymer of the present invention means a polymer that has tissue compatibility and blood compatibility and thus does not cause tissue rupture or blood coagulation due to the contact with the biological tissue or blood, and any polymer that can form a solid structure in which fine-grained calcium carbonate crystals are encapsulated by an emulsion method according to the present invention may be appropriately selected without a particular limitation.

In one embodiment of the present invention, the biocompatible polymer of the present invention is a polymer having a structure of polylactide (PLA), polyglycolide (PGA), polylactide-polyglycolide copolymer (PLGA), starch, glycogen, chitin, peptidoglycan, lignosulfonate, tannic acid, lignin, pectin, polyethylene glycol, polyethylene oxide, polyvinyl alcohol, polyethylene an oxide-polypropylene oxide block copolymer, cellulose, hemi-cellulose, heparin, hyaluronic acid, dextran, or alginate. Preferably, a polylactide-polyglycolide copolymer (PLGA) may be used.

In one embodiment of the present invention, the gas-generating nanoparticles of the present invention have a diameter of 100-250 nm. In addition, the diameter of the gas-generating nanoparticles is preferably 120-250 nm, more preferably 150-250 nm, and still more preferably 160-230 nm. The cell bursting effect that can lead to the necrotic cell death and the ultrasound imaging contrast effect can be maximized within the above diameter range.

Figure 13:
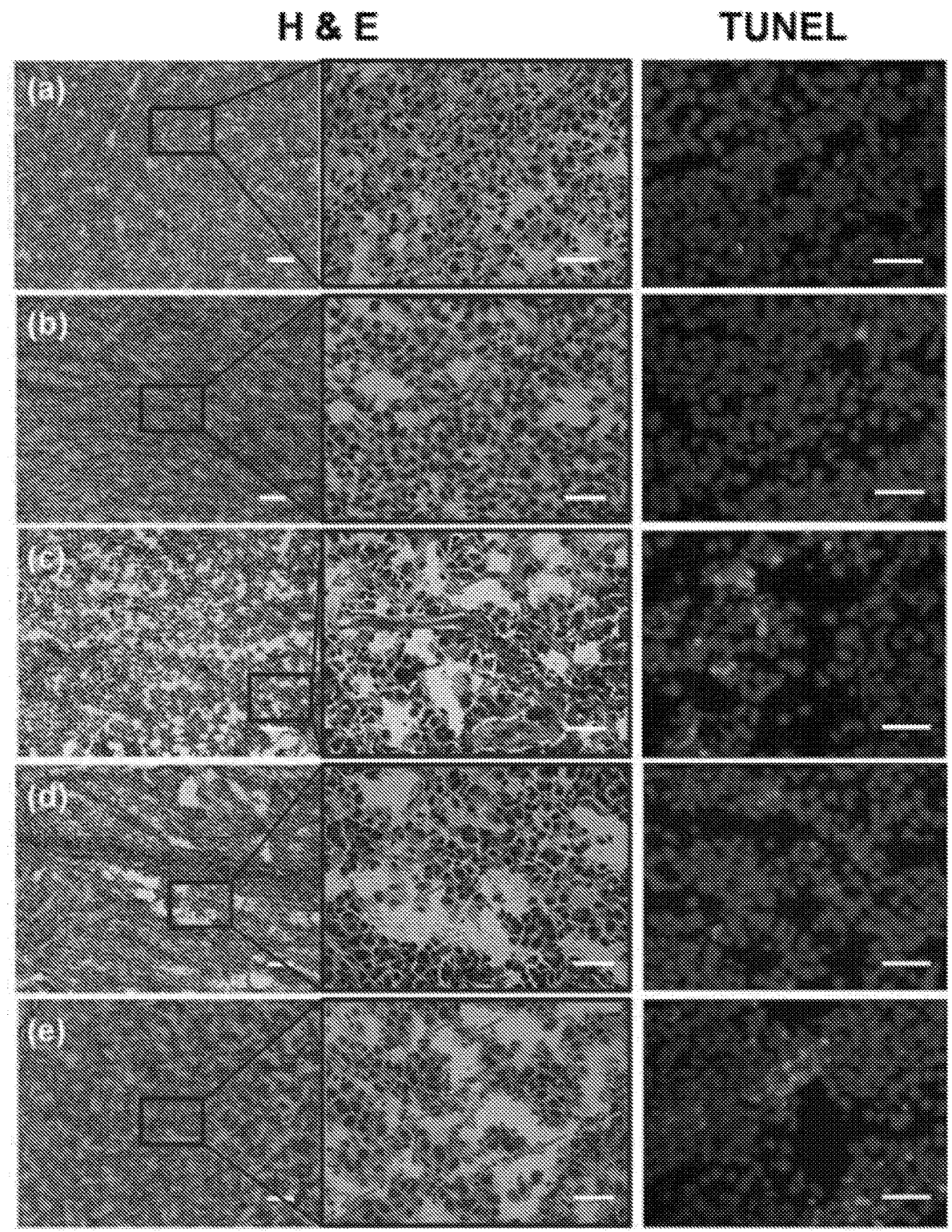
FIG. 13 shows H&E staining and TUNEL staining of tumor tissues retrieved from mice treated with (a) saline, (b) RVG-PNP, RVG-GNPs ((c) 0.01, (d) 0.1, and (e) 1) (scale bar=100 μm). The tumor tissues were embedded, frozen, and cut into 10 μm-thick sections at −20° C., and then stained with hematoxylin and eosin (H&E) and TUNEL assay. Arrows indicate necrotic cell bodies.

In one embodiment of the present invention, the weight ratio of the fine-grained calcium carbonate crystals and the biocompatible polymer is 0.001:1 to 1:1 (calcium carbonate: polymer). The weight ratio of the fine-grained calcium carbonate crystals and the biocompatible polymer is preferably 0.005:1 to 0.5:1, and more preferably 0.005:1 to 0.05:1. The fine-grained calcium carbonate crystals and the biocompatible polymer corresponding to the weight ratio can maximize the ultrasound imaging contrast effect and the cell bursting effect. The ratio of the fine-grained calcium carbonate crystals and the biocompatible polymer does not have a significant influence on the diameter of the generated gas-generating nanoparticles. The gas-generating nanoparticles prepared within the weight ratio range produced a significant tumor reduction effect in vivo (see FIG. 13). Considering that the increased content of the fine-grained calcium carbonate crystals greatly decreases the loading efficiency, the higher content than the above range cannot be expected, and the hard-shell structure by the biocompatible polymer may not be relatively strong. Meanwhile, in cases where the content of fine-grained calcium carbonate is still less than the above range, the amount of gas generated may be insufficient to obtain the imaging contrast effect and the cell bursting effect.

According to an aspect of the present invention, the present invention provides a composition for ultrasound imaging including gas-generating nanoparticles. The composition for ultrasound imaging of the present invention has an effect of releasing carbon dioxide specifically in acidic environment in vivo, and allows cancer cell tissue-specific imaging. In addition, differently from the conventional contrast agents, the present invention induces necrotic cancer cell death, thereby obtaining an imaging contrast effect and a cancer therapeutic effect.

According to an aspect of the present invention, the present invention provides a composition for cell necrosis induction using cell bursting due to the eruption of condensed gas, the composition containing gas-generating nanoparticles. The principle of the eruption of condensed gas is that, due to the hard-shell structure of the gas-generating nanoparticles of the present invention, the generated gas does not release to the outside simultaneously with the generation thereof, increasing the internal pressure of the gas-generating nanoparticles, and thus condensed and then explosively leaks.

According to an aspect of the present invention, the present invention provides a composition for drug delivery, in which a drug is loaded on the gas-generating nanoparticles. In addition to cell necrosis induction, the gas-generating nanoparticles of the present invention additionally load drugs therein and thus can be used as a composition for effective drug delivery. The composition for drug delivery of the present invention contributes to the maximization of drug efficacy through gas generation. The composition for drug delivery of the present invention improves an endosomal escape of drug through gas generation in the acidic environment, and especially, enables efficient delivery and efficacy maximization of gene drugs. The drug delivery systems of the prior art are required to secure pathways on which the gene drug can effectively escape from the endosome after the gene drug is delivered to the target site. In order to solve this, a cationic ligand (proton sponge effect) may be introduced and the volume of a surfactant may be increased. However, in the composition for drug delivery of the present invention, the generation of the fine-grained calcium carbonate gas contained inside the composition for drug delivery can improve the drug release rate, and since the improvement in the release rate is attained in the endosome- and lysosome-like environments (pH 4.0-6.0), the expression efficiency of the gene delivered to the target site is maximized.

The composition for drug delivery of the present invention can additionally obtain a therapeutic effect by the drug delivery as well as the introduction of necrotic cell death.

In one embodiment of the present invention, the drug of the present invention is a chemical drug, protein, peptide, or nucleotide. The chemical drug of the present invention is not particularly delimited, and thus any chemical drug that has an effect of inhibiting cancer cell generation, inhibiting or delaying cancer cell growth, treating cancer cells, inhibiting cancer cell metastasis due to migration and infiltration of cancer cells, or treating cancer stem cells may be used without limitation. The protein or peptide of the present invention is not particularly delimited, and examples thereof may include hormones, hormone analogues, enzymes, enzyme inhibitors, signaling proteins or fragments thereof, antibodies or fragments thereof, single chain antibodies, binding proteins or binding domains thereof, antigens, adhering proteins, structural proteins, regulatory proteins, toxin proteins, cytokines, transcription factors, blood coagulation factors, and vaccines, but are not limited thereto. More specifically, proteins or peptides delivered by the multifunctional complex of the present invention include insulin, insulin-like growth factor 1 (IGF-1), growth hormone, erythropoietin, granulocyte-colony stimulating factors (G-CSFs), granulocyte/macrophage-colony stimulating factors (GM-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRHII), gonadorelin, goserelin, histrelin, leuprorelin, lypressin, octreotide, oxytocin, pitressin, secretin, sincalide, terlipressin, thymopentin, thymosine α1, triptorelin, bivalirudin, carbetocin, cyclosporine, exedine, lanreotide, luteinizing hormone-releasing hormone (LHRH), nafarelin, parathormone, pramlintide, enfuvirtide (T-20), thymalfasin, and ziconotide.

According to an aspect of the present invention, the present invention provides a method for preparing gas-generating nanoparticles, the method including: (a) mixing a first water phase containing pulverized fine-grained calcium carbonate crystals with an oil phase containing a biocompatible polymer to form a water-in-oil (w/o) single emulsion; (b) mixing the emulsion of step (a) with a second water phase to a water-in-oil-in-water (w/o/w) double emulsion; and (c) solidifying the double emulsion of step (b).

In the method for preparing gas-generating nanoparticles of the present invention, as the "first water phase", an aqueous solvent (pH 7.0-8.0) containing fine-grained calcium carbonate slurry, specifically, for example, distilled water, physiological buffer solution (PBS), aqueous surfactant solution (aqueous PAV solution), or the like, may be used. As the "oil phase" in step (a) of the present invention, one in which the biocompatible polymer is dissolved in an organic solvent, which has strong hydrophobicity and volatility and is not mixed with the water phase, may be used, and specifically, for example, ones in which the biocompatible polymer is dissolved in methylene chloride, chloroform, dimethylformamide, ethyl acetate, acetone, acetonitrile, tetrahydrofurane, dimethyl sulfoxide, and a mixture solvent thereof, may be used. The mixing of the first water phase and the oil phase in step (a) of the present invention may be performed using, preferably, mechanical stirring, for example, an ultrasonic crusher, a homomixer, an agitator, or the like.

The single emulsion (w/o) prepared through step (a) of the present invention is mixed with the second water phase to form the double emulsion (w/o/w). As the second water phase, an aqueous surfactant liquid, specifically, for example, polyvinyl alcohol, poloxamer, or polyvinyl pyrrolidone may be used. The formed double emulsion may be solidified through evaporation or extraction of the organic solvent.

In one embodiment of the present invention, in the single emulsion in step (a) of the present invention, the weight ratio of the fine-grained calcium carbonate crystals and the biocompatible polymer is 0.001:1 to 1:1. Preferably, the weight ratio of the fine-grained calcium carbonate crystals and the biocompatible polymer is preferably 0.005:1 to 0.5:1, and more preferably 0.005:1 to 0.05:1.

The "method for preparing gas-generating nanoparticles" of the present invention is associated with a method for preparing "gas-generating nanoparticles" according to another aspect of the present invention, and descriptions of overlapping contents thereof will be omitted to avoid excessive complication of the specification.

Effect of the Invention

Features and advantages of the present invention are summarized as follows.

(a) The present invention provides gas-generating nanoparticles in which fine-grained calcium carbonate crystals are encapsulated inside the biocompatible polymer.

(b) The present invention provides a composition for ultrasound imaging, containing gas-generating nanoparticles.

(c) The present invention provides a composition for cell necrosis induction using cell bursting due to the eruption of condensed gas, the composition containing gas-generating nanoparticles.

(d) The present invention provides a composition for drug delivery, in which a drug is loaded on the gas-generating nanoparticles.

(e) The use of the gas-generating nanoparticles of the present invention can lead to the imaging and treatment of cancer cells at the same time.

(f) The use of the gas-generating nanoparticles of the present invention can lead to effective induction of necrosis of cancer cells.

(g) The use of the gas-generating nanoparticles of the present invention can lead to precise control of the content of calcium carbonate.

EXAMPLES

The present invention will be explained in more detail with reference to the following examples. It will be obvious to those skilled in the art that these examples are provided for illustrative purposes only and should not be construed as limiting the scope of the invention.

Materials and Methods

Example 1: Materials

RVG peptides (YTIWMPENPRPGTPCDIFTNSRG-KRASNG), derived by rabies virus glycoprotein, were purchased from the Tufts University Core Facility. RESOMER® RG 502H (MW 10,000, 0.16-0.24 dl/g) was purchased from Boehringer Ingelheim (Ingelheim, Germany). Poly (vinyl alcohol) (PVA, MW 27,000-32,000), dimethyl sulfoxide (DMSO), and 1-ethyl-3-(dimethylaminopropyl) carbodiimide (EDC), polyoxyethylenesorbitan monolaurate (Tween® 20), calcium carbonate ($CaCO_3$), calcium chloride (CaCl2), Fluorescein isothiocyanate-conjugated BSA (FITC-BSA), and 3-(4,5-dimethylthiazol-2-yl)-2,5-diphenyl tetrazolium bromide (MTT) were purchased from Sigma-Aldrich (Missouri, USA). N-hydroxysulfosuccinimide (sulfo-NHS) and sodium azide (99%, extra pure) were purchased from Thermo (CA, USA) and Acros Organics (Geel, Belgium), respectively. Methylene chloride (MC) was purchased from Wako Pure Chemical Industries Co (Osaka, Japan). Sodium hydroxide and hydrochloric acid were purchased from Duksan Pure Chemical Co (Ansan, Korea). 1,1'-Dioctadecyl-3,3,3',3'-tetramethylindocarbocyanine perchlorate (DiI) was purchased from Invitrogen (CA, USA). Duplexed siRNA were purchased from Genolution (Seoul, Korea). Dulbecco's modified Eagle's medium (DMEM), phosphate buffered saline (PBS), penicillin-streptomycin, trypsin-EDTA, and fetal bovine serum (FBS) were purchased from Gibco (NY, USA). The water was distilled and deionized using the Milli-Q System (MA, USA). Other reagents were also commercially available and used without further purification.

Example 2: Preparation and of Gas-Generating PLGA Nanoparticles and Surface Modification Gas-generating PLGA nanoparticles were prepared by the water-in-oil-in-water (w/o/w) double emulsion method. Briefly, 5% (w/v) PLGA was dissolved in MC. Calcium carbonate slurries with varying contents were prepared in the PBS (pH 7.4), homogenized by using a probe type sonicator (Branson Disital Sonifier®, CT, USA) for 60 s at 30 W output in the ice, added the PLGA solutions for varying weight ratios between the $CaCO_3$ and polymer ($CaCO_3$/PLGA=0-1, w/w). The solutions were emulsified by the sonicator for 60 s at 30 W output in 4° C. This single emulsion (w/o) was emulsified again into an aqueous 4% PVA solution by the sonicator for 120 s, leading to generating the double emulsion (w/o/w). The emulsion was poured into 1% PVA solution, mixed by a mechanical stirrer at 600 rpm, and solidified the hardened nanoparticles. Finally, un-encapsulated $CaCO_3$ were removed by washing 5 times and filtering (0.22 μm syringe filter; Millipore, MA, USA), and then the gas-generating nanoparticles were collected by a freezing dryer (LABCONCO, MO, USA).

It previous verified was effect of the RVG peptide on neuroblastoma-specific targeting efficiency and optimized its surface modification onto the PLGA nanoparticles using the carbodiimide mechanism. Briefly, the gas-generating nanoparticles (0.5 mM) were suspended in 0.1 M MES buffer (pH 7.0), and EDC (0.5 mM) and Sulfo-NHS (0.25 mM) were added to the suspension in order to pre-activate the carboxylic groups of nanoparticles. The NHS-activated nanoparticles then were reacted with ethylene diamine (0.5 mM) for overnight. The resulting nanoparticles were separated and washed three times with deionized water, and freeze-dried. The functionalized gas-generating nanoparticles with primary amine were re-suspended in the MES buffer (pH 7.0), and then EDC/Sulfo-NHS and RVG peptide were added to the suspension (RVG/PLGA=1, mol/mol). RVG peptide-conjugated nanoparticles (RVG-PNP) and gas-generating nanoparticles (RVG-GNPs (0.01-1)) were collected, washed with deionized water, and then stored in 4° C.

Example 3: Characteristics of Gas-Generating Nanoparticles

The nanoparticles (PLGA-NPs) and gas-generating nanoparticles (PLGAGNPs) dissolved with a 1N NaOH solution, immediately neutralized with a 1 N HCl solution to determine loading contents of $CaCO_3$ contents. Calcium carbonate minerals at the solution were dissociated in acidic buffer (sodium acetate buffer, pH 5.5), and their calcium ions were examined using a Calcium colorimetric assay kit (BioVision, CA, USA). Releasing profiles of calcium ions from the nanoparticles in different release media (pH 5.5 and 7.4) were examined, respectively. The nanoparticles (3 mg/ml) were suspended in release media (PBS pH 5.5 and 7.4) containing 0.02% sodium azide and 0.02% Tween® 20, and placed in a horizontally shaking water bath (200 rpm, 37° C.). The release buffer (0.01 ml) was withdrawn at predetermined time intervals, and releasing calcium ion contents were analyzed by using the Calcium colorimetric assay kit.

The size and its distribution of the PLGA nanoparticles with or without the calcium carbonate at neutral and acidic environments (pH 7.4 and 5.5) was determined by using a Zetasizer nano ZS (Malvern Instr., Malvern, UK), respectively. Measurements were performed in distilled water adjusted with sodium chloride to a conductivity of 50 μS/cm at a temperature of 25° C. The changes in morphologies of the nanoparticles were dispersed in neutral (pH 7.4) and acidic buffers (pH 5.5) was observed by scanning electron microscopy (S-4800 UHR FE-SEM; Hitachi, Tokyo, Japan). A suspension of nanoparticles in the buffer was mounted on aluminum holders at room temperature, freezing-dried, and then coated with platinum while under a vacuum.

The nanoparticles (PLGA-NP) and gas-generating nanoparticles (PLGAGNP1) containing FITC-BSA as model drug were next prepared. In order to determine loading contents of the model drugs encapsulated in the nanoparticles, they were dissolved with a 1N NaOH solution, immediately neutralized with a 1 N HCl solution, and filtered through a 0.2 μm filter (Millipore, MA, USA). Loading efficiency was expressed as the ratio between the actual contents of the nanoparticles and the amount initially added to the nanoparticles. Release profiles of the drugs from the nanoparticles in different release media (pH 5.5 and 7.4) were examined, respectively. The nanoparticles (10 mg) were suspended in 20 ml release media (PBS pH 6.0 and 7.4) containing 0.02% sodium azide and 0.02% Tween® 20) placed in a horizontally shaking water bath (200 rpm, 37° C.). At predetermined time intervals, supernatant was separated by centrifugation, a sample (0.1 ml) was withdrawn, and fresh media was added to replace it. All of the FITC-BSA contents were analyzed by an UV/VIS spectroscopy (SpectraMax M2$^e$, CA, USA) ($\lambda_{ex}$=495 nm and $\lambda_{em}$=515 nm).

Example 4: Cytotoxicity

Cytotoxicity of the PLGA-GNPs for various cell lines, neuroblastoma (N2a), lung epithelial cell (MLE12), cardiomyoblast (H9c2), and fibroblasts (NIH3T3) was identified by MTT viability cell assay. The cell lines were cultured in a DMEM media (10% FBS, 1% penicillin streptomycin), and it from passage two to three were used for all experiments. The cells were seeded onto 96-well tissue culture plates ($5\times10^3$ cells/well) and incubated for 12 h at 37° C. under 5% $CO_2$ atmosphere. The PLGA-GNPs (500 μg/well) with varying the $CaCO_3$ contents ($CaCO_3$/PLGA=0-1, w/w) were added to the wells and incubated for 48 h. The cells were washed with PBS three times, and MTT solution (50 μg/ml) was added to each well. After incubation for 3 h generated formazan crystals were dissolved in DMSO, and its absorbance was measured at 540 nm with the UV/VIS spectroscopy. It was also evaluated the cytotoxicity of calcium and bicarbonate ions were generated by the GNP1 as well as equal contents of a $CaCO_3$ solution. The GNP1 and $CaCO_3$ mineral were dissolved in a sodium acetate buffer (0.1 M sodium acetate, pH 5.5), and quickly treated into the N2a cells.

Example 5: In Vitro Ultrasound Imaging

Ultrasound (US) imaging was performed at the static state in a phantom study in vitro using an Acuson Sequoia 512 system (Siemens Medical Solutions, Malvern, Pa., USA). The phantom was prepared by embedding PCR tubes in agarose gel (3%, w/v). The RVG-GNPs, which suspended in pH 7.4 PBS buffer ([nanoparticle]=1-10 mg/ml), were placed into the phantoms, and then an acid buffer (sodium acetate buffer) was added. The US imaging was monitored using a 15 MHz probe (Acuson model15 L8), and performed in the 2D mode. The RVGPNP with the equal conditions was used to negative control.

Example 6: In Vivo Ultrasound Imaging

Tumor-specific in vivo ultrasound imaging of the RVG-GNPs was next investigated. Six-week-old, male athymic mice (20 g body weight, Orient Lab Animal, Sungnam, Korea) were anesthetized by intraperitoneal injection of Zoletil (35 mg/kg)/Rompun (2 mg/kg). Tumor-bearing mice were established by subcutaneously inoculating N2a cells ($1.0 \times 10^6$/mice) onto the backs of the mice. When the tumors grew to about 100 mm$^3$ volumes, RVG-PNP, RVG-GNP0.01, and RVG-GNP1 were intravenously injected into the mice (50 mg/kg). All of the procedures were in compliance with Hangyang University Guidelines for the care and use of laboratory animals. Ultrasound imaging of the nanoparticles was obtained with the Acuson Sequoia 512 system in the predetermined intervals.

Example 7: Effect of RVG-GNPs on Necrotic Cell Death

Effect of burst $CO_2$ generation from the RVG-GNPs on cell death by either apoptosis or necrosis was next analyzed by using a Roche Annexin-V-FLUOS Staining Kit (Roche, Indianapolis, Ind., USA). N2a cells were placed on 8-well chamber slides ($5 \times 10^3$ cells/well) and treated with the RVG-GNPs. After 24 h the media were removed, washed with PBS three times, stained with Annexin-VFITC antibody and Propidium Iodide (PI) as markers of apoptotic and necrotic cell death, and then fixed with 2% formaldehyde. The slides were mounted by mounting medium with 4',6'-diamino-2-phenylindole (DAPI, Vectashield, CA, USA) and analyzed by fluorescence microscopy (TE2000-E; Nikon, Kanagawa, Japan). In order to quantify comparison of apoptosis and necrosis, the stained cells were analyzed by the flow cytometer for fluorescence intensity in FL-1 (Annexin-V-FITC) and FL-2 (PI). Morphologies of the cells were also observed by optical microscopy (AcquCAM II; Olympus, Tokyo, Japan).

Caspase-3 activation, one of apoptotic pathways for cell death, was measured by a Caspase-Glo® 3/7 assay (Promega, WI, USA). The N2a cells were placed on white-walled 96-well plate (SPL Life Science, Pocheon, Korea) and treated with the RVG-PNP and RVG-GNPs for 24 h. The cells were washed with PBS three times, treated with 200 μl of detection solution (reagent/buffer=1/1, v/v). After 3 h, the luminescence intensities of the solution from each well were measured using a luminometer (Orion II Microplate Luminometer; Berthold Detection System, Pforzheim, Germany). Relative luminescence values were normalized the intensity of non-treated solution, and Docetaxel (LC Laboratories, Woburn, USA), which was induced apoptotic cell death, was used as positive control.

Example 8: Effect of RVG-GNPs on Carcinoma Viability

N2a cells were seeded onto 24-well tissue culture plates ($2 \times 10^3$ cells/well) and incubated for 12 h at 37° C. under 5% $CO_2$ atmosphere. The RVG-GNPs (500 μg/ml) were daily added to the wells and incubated for 7 days. At each predetermined time interval, the cells were washed with PBS three times, and MTT solution (50 μg/ml) was added to each well. After incubation for 3 h generated formazan crystals were dissolved in DMSO, and its absorbance was measured at 540 nm with the UV/VIS spectroscopy. Growth rates were calculated from number of cells at 7 days to the number at day 0. It was also compared the cytotoxicity treated gas-generating nanoparticles (GNP0.01 and GNP1; no conjugation of RVG peptide), RVG-conjugated nanoparticles containing $CaCl_2$ (no generating gas), a $CaCl_2$ solution, a $CaCO_3$ solution which dissolved a sodium acetate buffer (0.1 M sodium acetate, pH 5.5), was used as negative control.

Example 9: Anti-Cancer Efficacy in a Tumor-Bearing Mouse Model

In order to verify anti-cancer efficacy of the burst $CO_2$ generation from RVGGNPs, tumor-bearing mice model were prepared as above described (n=8). Tumor-bearing mice were divided into four groups treated with saline (control), the RVG-PNP, RVG-GNP0.01, RVG-GNP0.1, and RVG-GNP1 (10 mg/kg polymer/mice; five injections for 1 week). Changes in tumor volume calculated using a formula ((long axis×short axis$^2$)/2) for 2 weeks. The tumor tissues were retrieved 2 weeks after the first injection, weights, embedded into an optimal cutting temperature compound (TISSUE-TEK® O.C.T. compound; Sakura Finetek, CA, USA), frozen, and cut into 10 μm-thick sections at −20° C. The tissue sections were stained with hematoxylin and eosin (H&E), in addition, apoptosis in the tissues was identified using an Apoptosis Detection Kit (ApopTag® Red In Situ, Millipore; Billerica, Mass., USA), according to the manufacturer's instructions.

Example 10: Statistical Analysis

All data are presented as mean±standard deviation. Statistical analyses were performed using Student's t-test. *P-values <0.05, P-values <0.01, and *P-values <0.001 were considered statistically significant.

Results

1. Preparation and Characteristics of Gas-Generating Nanoparticles

PLGA nanoparticles containing calcium carbonate mineral ($CaCO_3$) as a carbon dioxide-generating agent, were fabricated by the double emulsion method.

The gas-generating PLGA nanoparticles with varying calcium carbonate contents (0.01-1) were prepared, and loading contents were 0.0072, 0.089, and 0.24, respectively. All of the gas-generating PLGA nanoparticles were obtained with preparative yield of more than 60%. The mean diameter of the nanoparticles was approximately 180 nm, irrespective of calcium carbonate contents (Table 1). All of them showed low polydispersity index (PDI) values, indicating a narrow size distribution. The mean diameter of gas-generating nanoparticles at the acidic condition was generally increased, while that of PLGA nanoparticles without $CaCO_3$ were not significantly influenced. SEM images proved spherical shape of the nanoparticles at the neutral condition (FIG. 1; left), but destroyed structures of PLGA-GNPs were observed at the acidic condition (FIG. 1; right), likely due to generation of $CO_2$ gas bubbles. Interestingly, the particles size went up to microns for PLGA-GNP0.01, despite of the smallest $CaCO_3$ content. It might be implied to burst generation of gas bubbles from the nanoparticles.

TABLE 1

| Sample | Ideal loading content (CaCO$_3$/PLGA; w/w) | Actual loading contents (CaCO$_3$/PLGA; w/w) | Size (mm) | PDI |
|---|---|---|---|---|
| PNP | 0 | 0 | 182.8 | 0.029 |
| GNP0.01 | 0.01 | 0.007 | 183.1 | 0.036 |
| GNP0.1 | 0.1 | 0.089 | 182.1 | 0.029 |
| GNP1 | 1 | 0.240 | 181.6 | 0.028 |

2. pH-Sensitive Behaviors of Gas-Generating Nanoparticles PLGA Nanoparticles

Figure 2:
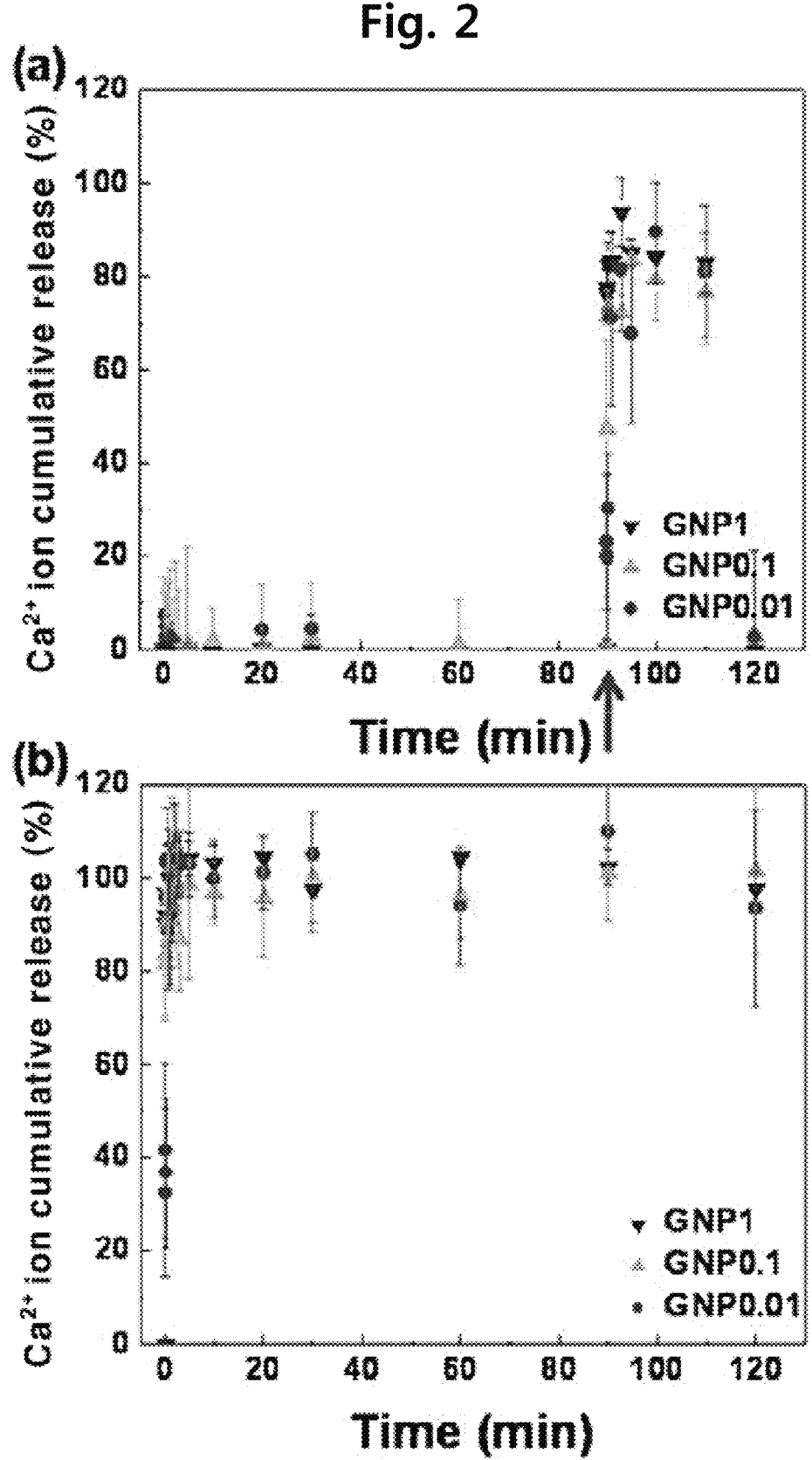
FIG. 2 shows In vitro calcium ion release from gas-generating nanoparticles at (a) neural (pH 7.4) and (b) acidic (pH 5.5) conditions. Arrow indicates adjustment of pH to 5.5 by adding acidic buffer. Gas-generating nanoparticles were suspended in release media (3 mg/ml), and the amount of released calcium ions were quantified at predetermined time intervals.

The release profile of calcium ions from gas-generating nanoparticles at acidic and neutral conditions was monitored for 2 h in vitro. The release of calcium ions from the nanoparticles was very little at the neutral condition (FIG. 2a). However, initial burst release of the ions was observed at the acidic condition depending on encapsulated CaCO$_3$ contents (FIG. 2b). The burst release of calcium ions from the nanoparticles was monitored when acidic buffer was added to the neutral condition (FIG. 2a; arrow).

Figure 3:
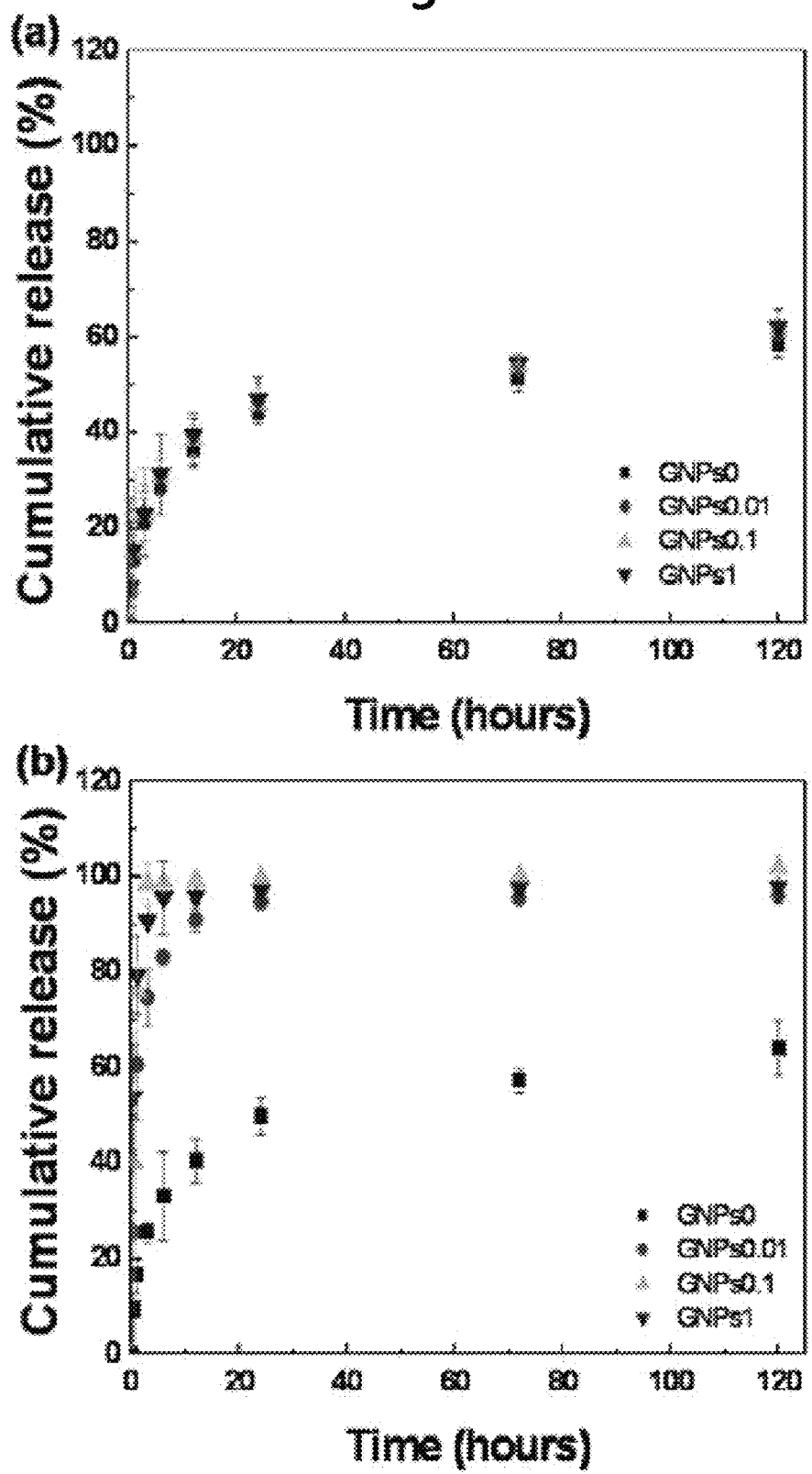
FIG. 3 shows In vitro BSA release from gas-generating nanoparticles at (a) neural (pH 7.4) and (b) acidic (pH 5.5) conditions. Gas-generating nanoparticles containing FITC-BSA were suspended in release media (0.5 mg/ml), and the BSA content was determined at predetermined time intervals.

The effect of generation of gas-bubbles on the release behavior of model proteins from the nanoparticles was next investigated (FIG. 3). The loading efficiency of proteins into PLGA nanoparticles was not significantly influenced by the CaCO$_3$ contents (about 80%), and the protein release from the nanoparticles was not affected by the CaCO$_3$ contents at the neutral condition for 5 days. In contrast, the most of proteins were released from the gas-generating nanoparticles at the acidic condition within 1 day. There was no difference between the release behavior of proteins from the nanoparticles without the CaCO$_3$ either at the acidic condition or neutral condition.

3. Cell Viability of the Gas-Generating Nanoparticles

Figure 4:
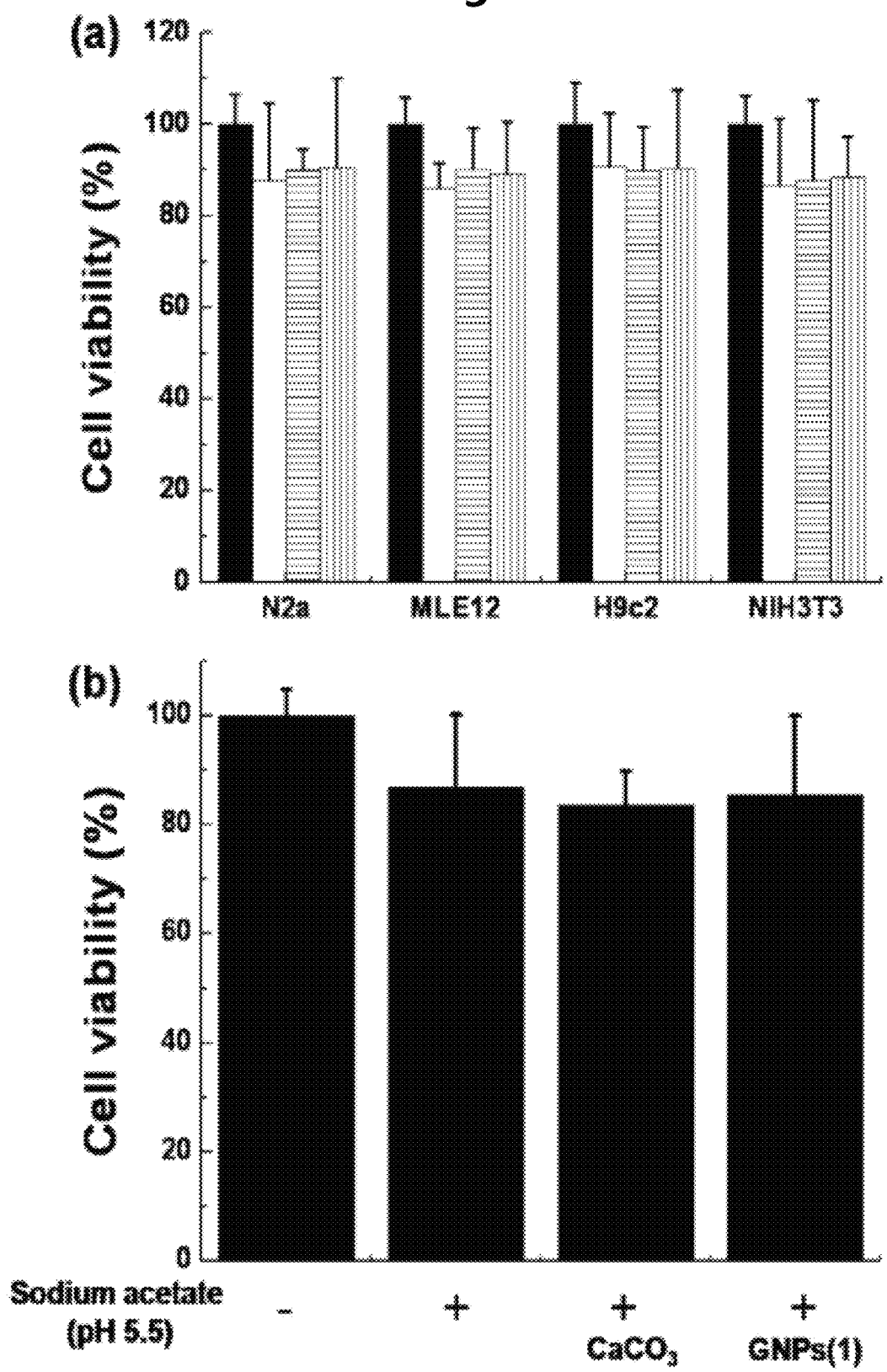
FIG. 4 shows cytotoxicity of (a) GNPS with different $CaCO_3$ contents (0, filled bar; 0.01, empty bar; 0.1, horizontal line-filled bar; and 1, vertical line-filled bar) in various type of cells and (b) calcium and bicarbonate ions in N2a cells. Cells were placed on a 96-well tissue culture plate ($5 \times 10^3$ cells/well) and treated with gas generating nanoparticles ([GNPs]=500 μg/ml, pH 7.4) and calcium and bicarbonate ions ([GNP1]=[$CaCO_3$]=500 μg/ml, sodium acetate buffer (pH 5.5)) for 48 h. Cell viability was determined by MTT assay.

Viability of cells treated with gas-generating nanoparticles containing different CaCO$_3$ contents (PLGA-GNPs, no RVG conjugation) was investigated by MTT assay. No significant cytotoxicity of gas-generating nanoparticles was observed up to polymer concentration of 500 μg/ml (FIG. 4a). Toxicity of calcium and bicarbonate ions along with carbon dioxide gas generated from the nanoparticles was next evaluated. The cells were slightly affected by low pH condition (sodium acetate; pH 5.5). However, the released ions did not influence the cell viability, suggesting possible application of gas-generating nanoparticles to non-toxic contrast agent (FIG. 4b).

4. Ultrasound Imaging

Figure 5:
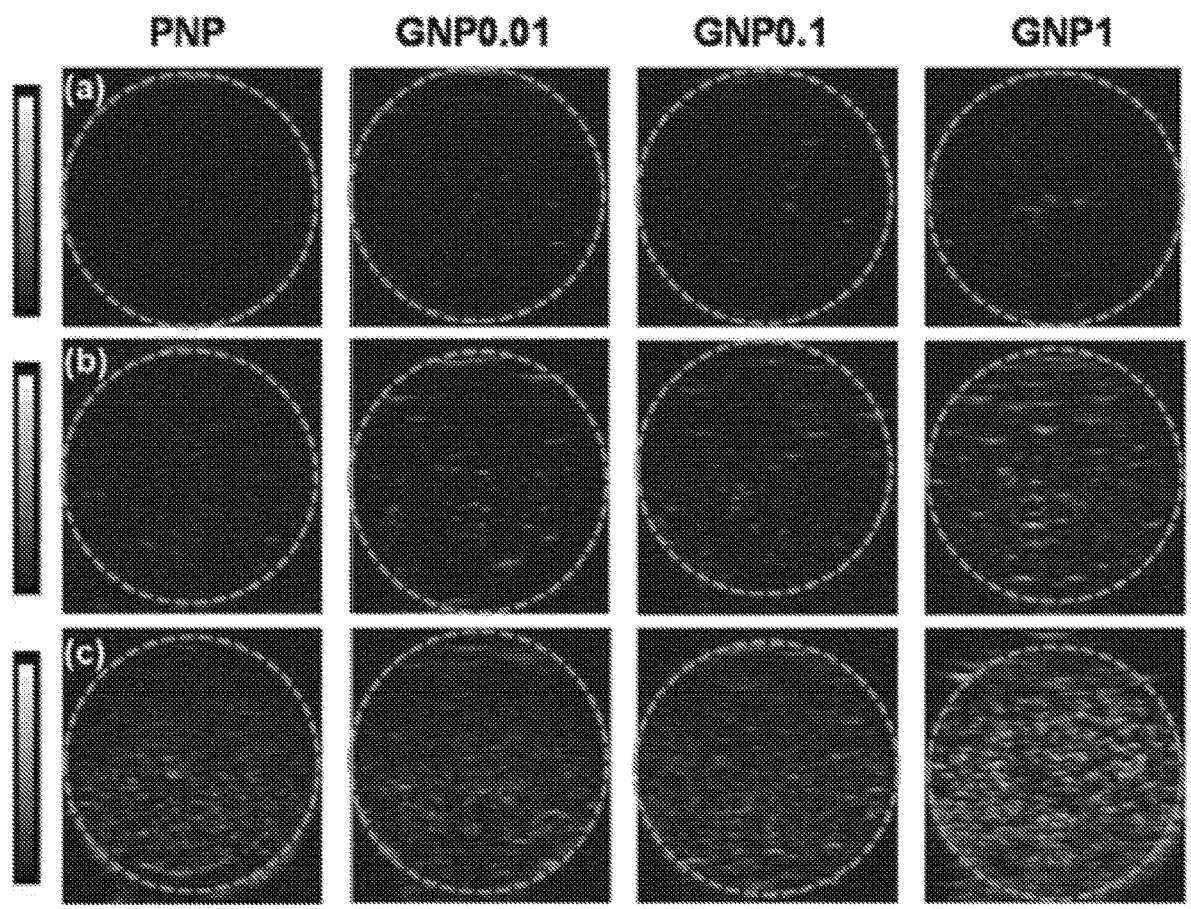
FIG. 5 shows In vitro ultrasound signals of PLGA NPs and PLGA-GNPs (0.01-1) at the acidic condition (pH 5.5). ([nanoparticle]=(a) 1, (b) 5, and (c) 10 mg/ml). The gas-generating nanoparticles were suspended in PBS buffer (pH 7.4) and then ultrasound images were taken after an acid buffer (sodium acetate buffer) was added (final pH 5.5).

It was tested whether gas-generating nanoparticles could be utilized as ultrasound contrast agents (FIG. 5). PLGA nanoparticles, which do not generate CO$_2$ gas, showed no ultrasound contrast signal under the acidic environment. In contrast, the contrast signal was enhanced for gas-generating nanoparticles and the signal intensity increased as the CaCO$_3$ contents increased. The increased concentration of the nanoparticles also enhanced the contrast signal.

Figure 6:
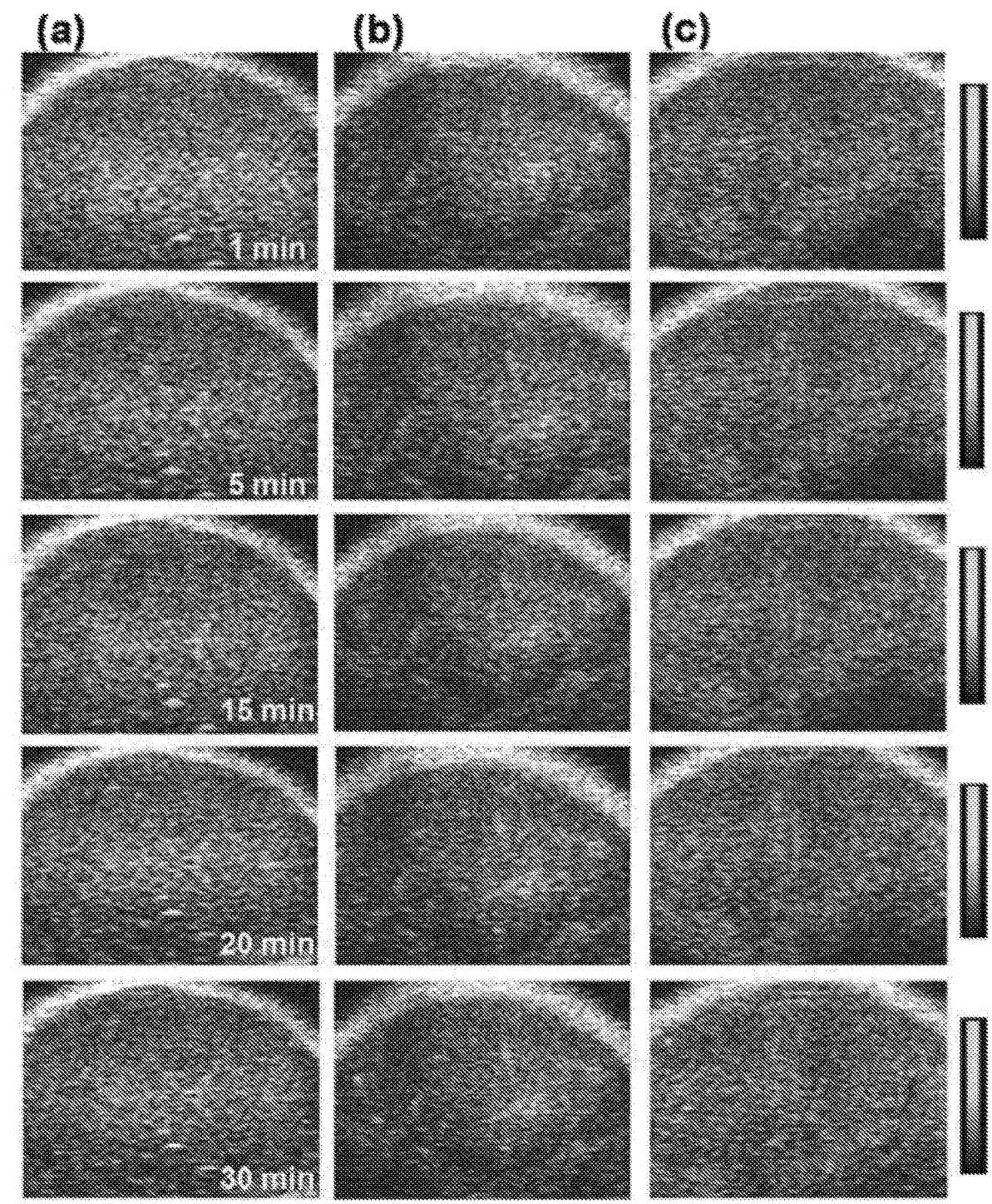
FIG. 6 shows In vivo ultrasound signals at the tumor site were observed at the predetermined time intervals after (a) RVG-PNP, (b) RVG-GNP0.01, and (c) RVG-GNP1 were intravenously injected into the mice (25 mg/kg polymer/mouse).

In vivo ultrasound imaging study was next carried out using a neuroblastoma-bearing mouse model (FIG. 6). Gas-generating nanoparticles were conjugated with the RVG peptide onto the surface of the nanoparticles (RVG/PLGA=1, mol/mol). RVG-conjugation did not influence the characteristics of the nanoparticles. Gas-generating nanoparticles modified with RVG peptide (RVGGNPs) also showed neuroblastoma-targeting specificity as discussed in the previous section. After intravenous injection, few ultrasound signals in the mice treated with RVG-conjugated nanoparticles (no CaCO$_3$) were observed at the tumor site. In contrast, signals were clearly monitored when gas-generating nanoparticles were injected in the mice. Interestingly, the signals at the tumor site of mice treated with RVG-GNP0.01 appeared similar to that of RVG-GNP1, despite of low CaCO$_3$ contents.

5. Effect of RVG-GNPs on Carcinoma Necrosis

Figure 7:
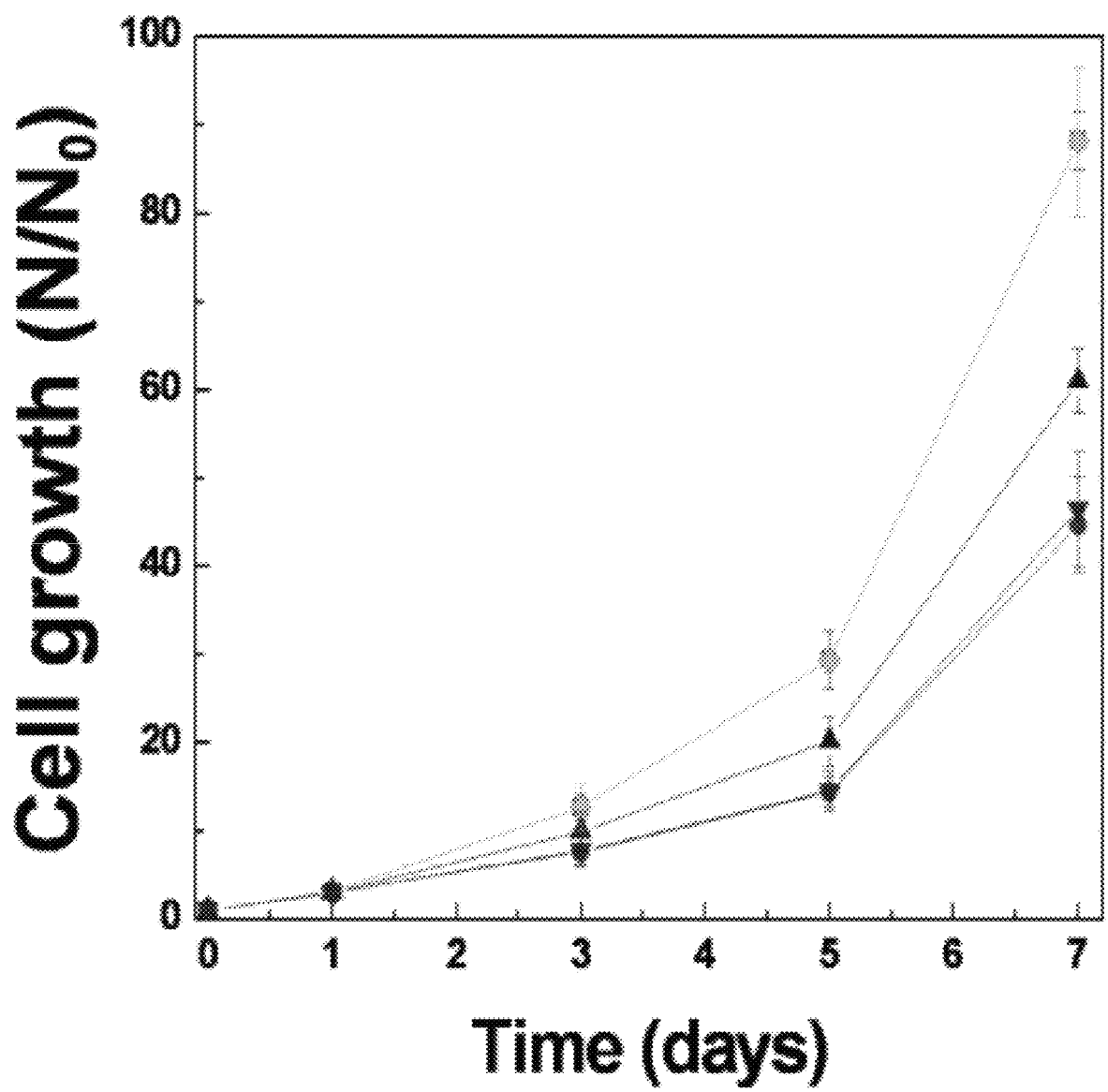
FIG. 7 shows In vitro growth of neuroblastoma cells treated daily with media only (square), RVG-PNP (diamond), RVG-GNP0.01 (circle), RVG-GNP0.1 (triangle), and RVG-GNP1 (inverted triangle). N2a cells were placed on a 24-well tissue culture plate ($2 \times 10^3$ cells/well), and nanoparticles were added daily to the wells for 7 days ([nanoparticle]=500 μg/ml).

It was verified that gas-generating nanoparticles, which were associated into the carcinoma, suppressed cell growth. An RVG-conjugated PLGA nanoparticle (RVG-PNP) with neuroblastoma specificity was constructed as above described. Gas-generating nanoparticles were modified with the RVG-peptide onto their surface, and utilized to treat N2a cells daily for 7 days (FIG. 7). The cell growth was slowing down as the gas-generating nanoparticles (RVG-GNPs) were used. Both RVG-GNP0.01 and RVG-GNP1 showed excellent suppression of cell growth regardless of CaCO$_3$ contents. The growth rates similar to non-treated group was obtained when non-modified gas-generating nanoparticles (GNPs) were used to treat the cells, indicating no significant cytotoxicity for long-time periods. In addition, calcium and bicarbonate ions generated from the nanoparticles along with the CO$_2$ gas did not significantly influence the cell growth (Table 2).

TABLE 2

| Sample | Treatment system | Loading agents | Growth rate (day$^{-1}$) |
|---|---|---|---|
| Control | — | — | 0.923 ± 0.007 |
| RVG-PNPs (CaCl$_2$(1)) | RVG-PNP | CaCl$_2$(1) | 0.910 ± 0.009 |
| GNP0.01 | PLGA-PNP | CaCO$_3$(0.01) | 0.925 ± 0.015 |
| GNP1 | PLGA-PNP | CaCO$_3$(1) | 0.938 ± 0.011 |
| Soluble CaCl$_2$(1) | — | CaCO$_2$(1) | 0.943 ± 0.017 |
| Soluble CaCO$_3$(1) | — | CaCO$_3$(1) | 0.923 ± 0.006 |

Table 2 shows growth rates of neuroblastoma cultured under various conditions. N2a cells were placed on a 24-well tissue culture plate (2×10$^3$ cells/well), and nanoparticles were added daily to the wells for 7 days. ([nanoparticle]=500 μg/ml; [CaCl$_2$]=[CaCO$_3$]=250 μg/ml).

Figure 8:
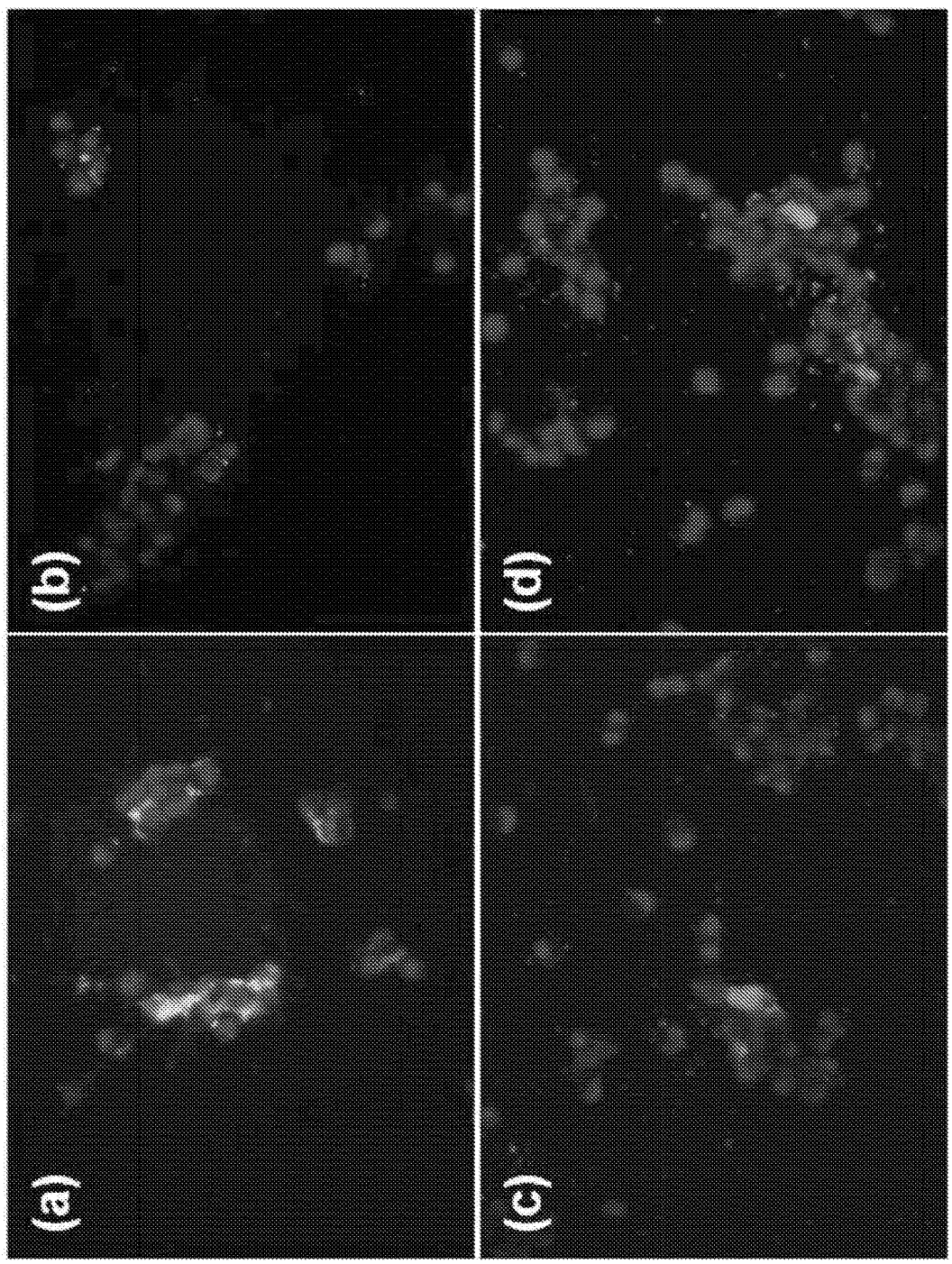
FIG. 8 shows fluorescence microscopy images of N2a cells treated with (a) docetaxel, (b) RVG-PNP, (c) RVG-GNP0.01, and (d) RVG-GNP1. N2a cells were placed on a 8-well chamber slide ($5 \times 10^3$ cells/well) and treated with nanoparticles for 12 h ([nanoparticle]=500 μg/ml and [docetaxel]=2 mg/ml). Blue, green, and red colors represent DAPI, Annexin-V, and PI, respectively.
Figure 9:
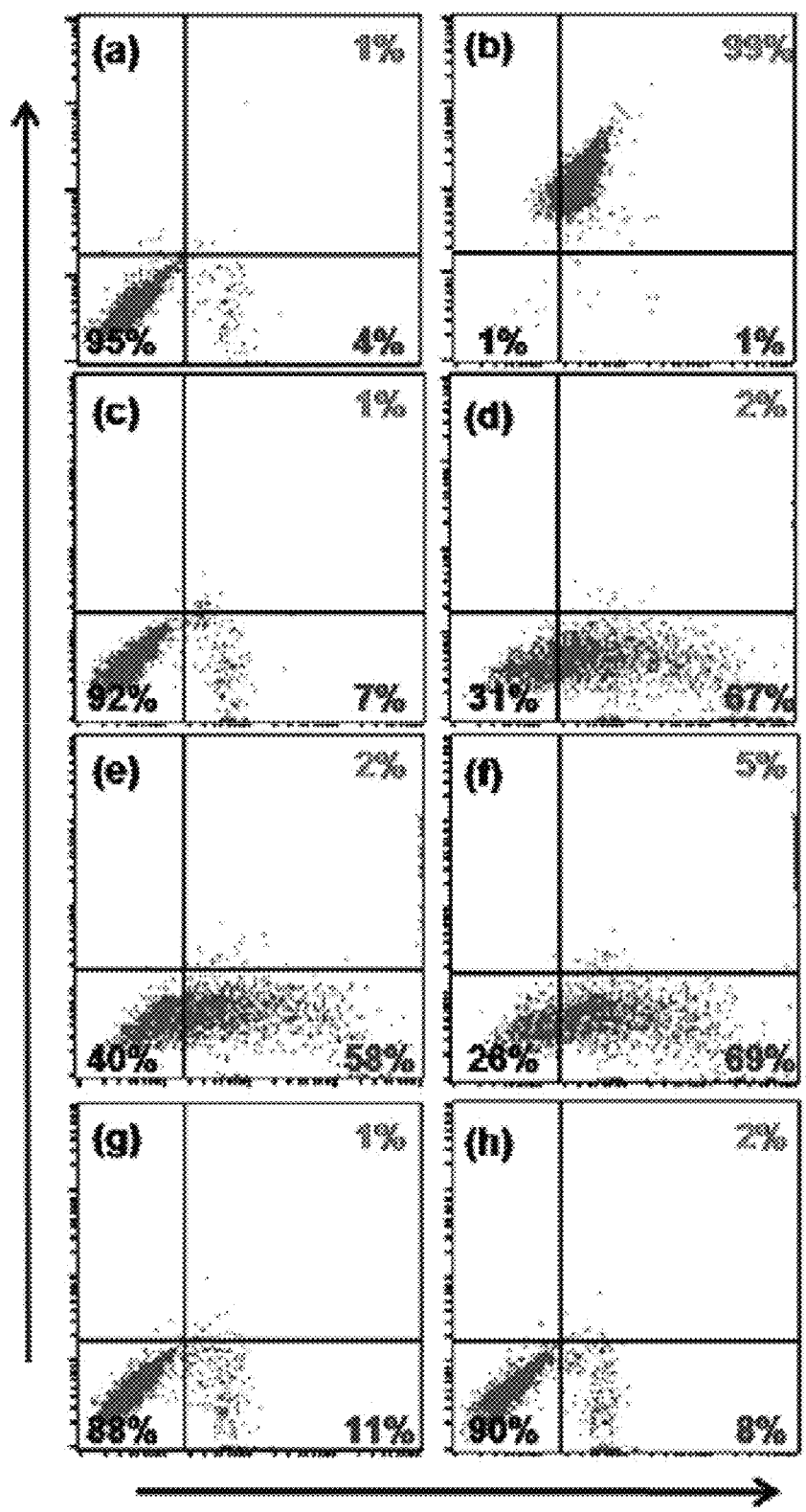
FIG. 9 shows flow cytometric analysis of apoptosis and necrosis of N2a cells treated with (a) saline, (b) docetaxel, (c) RVG-PNP, (d) RVG-GNP0.01, (e) RVGGNP0.1, (f) RVG-GNP1, (g) RVG-PNP ($CaCl_2$), and (h) GNP1 (no peptide). N2a cells were placed on a 12-well tissue culture plate ($1 \times 10^5$ cells/well) and treated with nanoparticles for 12 h ([nanoparticle]=500 μg/ml and [docetaxel]=2 mg/ml). Annexin-V and PI indicate apoptosis (green) and necrosis (red), respectively.
Figure 10:
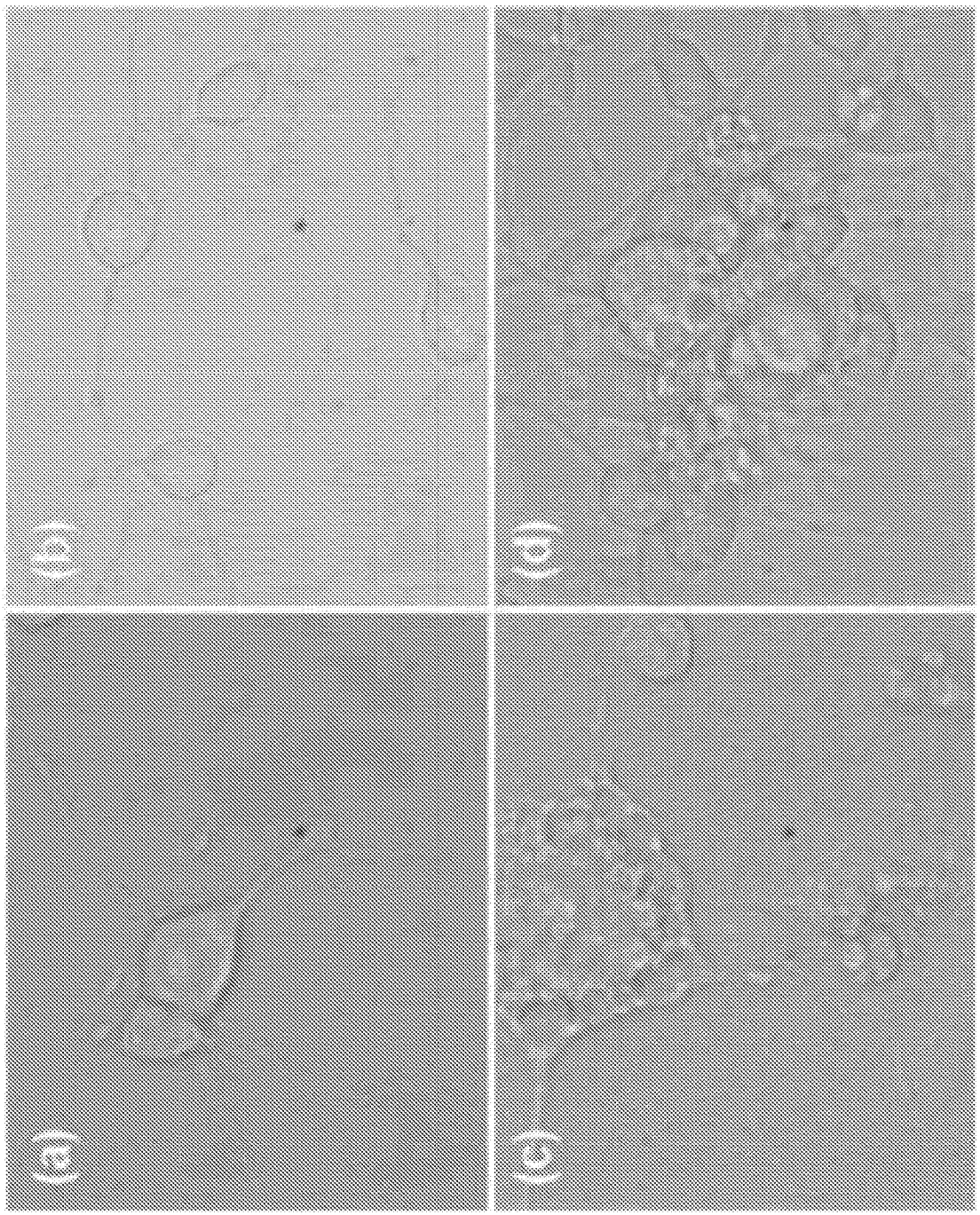
FIG. 10 shows optical microscopic images of cells treated with (a) RVG-PNP and RVG-GNPs ((b) 0.01, (c) 0.1, and (d) 1). N2a cells were placed on a 8-well chamber slide ($5 \times 10^3$ cells/well) and treated with nanoparticles for 12 h ([nanoparticle]=500 μg/ml).
Figure 11:
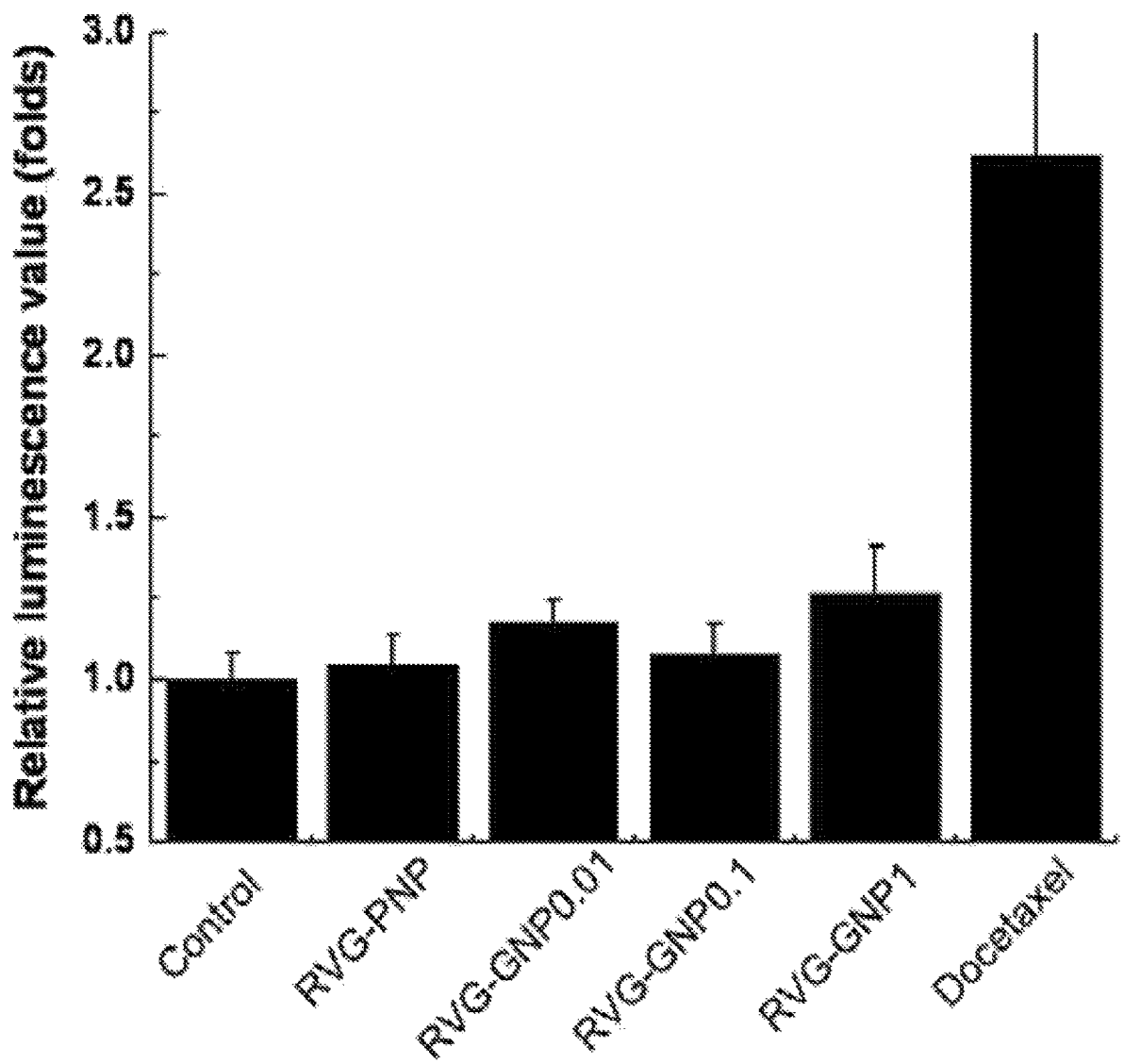
FIG. 11 shows effect of gas-generating nanoparticles on induction of apoptotic pathways. N2a cells were placed on a 96-well tissue culture plate ($5 \times 10^3$ cells/well) and treated with nanoparticles for 12 h ([nanoparticle]=500 μg/ml, [docetaxel]=2 mg/ml), and amounts of activated caspase-3 in the cells were determined.

It was next tested whether the suppression of cell growth was caused by apoptotic or necrotic cell death. Either apoptotic or necrotic cell death was distinguished using Annexin-V/PI assay. FITC-labeled Annexin-V and propidium iodide (PI) indicate apoptosis and necrosis, respectively. Numerous red fluorescence signals were observed in the cells treated with gas-generating nanoparticles, while predominant green fluorescence signals were observed for the cells treated with docetaxel (FIG. 8). In flow cytometric analysis, cells treated with gas-generating nanoparticles showed necrotic cell population, clearly indicating necrotic cell death was induced by the gas-generating nanoparticles (FIG. 9). However, the necrotic cell population was independent of CaCO$_3$ contents. Much vacuolation of cellular structures were observed in the cells treated with gas-generating nanoparticles, compared with non-gas-generating nanoparticles (FIG. 10). Caspase activation, as general apoptotic pathway, induces a caspase cascade and finally leads to a cellular apoptosis [The Journal of Cell Biology 1999; 144(2):281-292]. Docetaxel-mediated apoptosis, which is known to induce FAK cleavage and activation of caspase-3, has been exploited to cancer therapy [The Journal of Cell Biology 1999; 144(2):281-292]. Significant caspase-3 activation was observed for N2a cells treated with docetaxel. Surprisingly, the cells treated with the gas-generating nanoparticles did not show increase of activation (FIG. 11).

6. In Vivo Therapeutic Efficacy of RVG-GNPs

Figure 12:
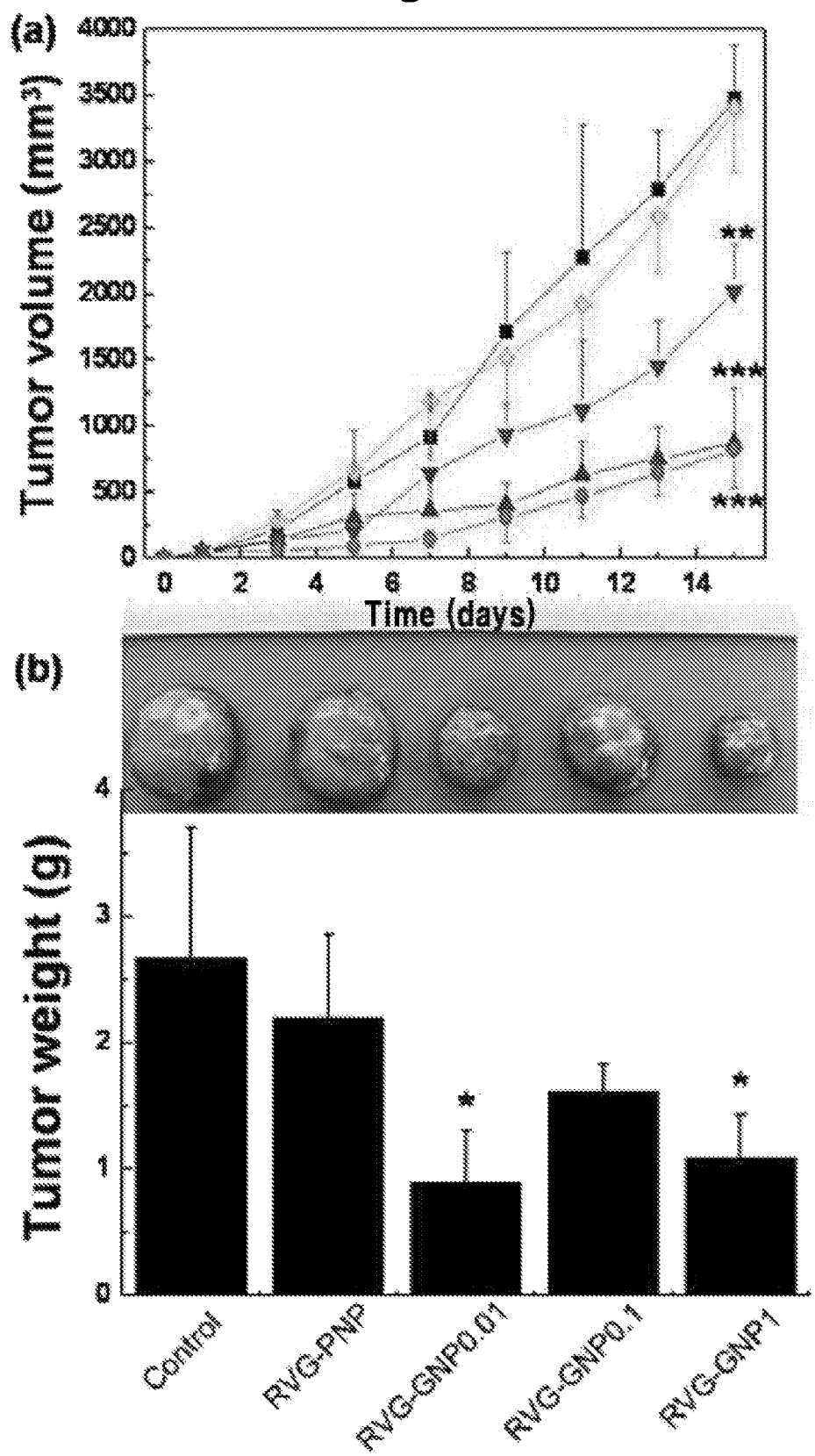
FIG. 12 shows (a) Changes in tumor volume and (b) final tumor weight of mice treated with saline (square), RVG-PNPs (diamond), and RVG-GNPs (0.01, triangle; 0.1, inverted triangle; and 1, circle) (10 mg/kg polymer/mouse and 20 mg/kg docetaxel/mouse; five intravenous injections during 1 week).

Therapeutic efficacy of RVG-conjugated gas-generating nanoparticles was next evaluated using a neuroblastoma-bearing mouse model. When the tumor volume of each mouse reached approximately 50 mm$^3$, RVG-GNP0.01, RVGGNP0.1, and RVG-GNP1 were intravenously injected into the mice and changes in tumor volume were monitored for 2 week (FIG. 12). Tumor-bearing mice were also treated with either saline or RVG-conjugated PLGA nanoparticles (RVG-PNP, no gas generation) as a control. The mice treated with saline only showed tremendous tumor growth up to 3,000 mm$^3$. No effect of RVG-PNP on suppression of tumor growth was also observed. Surprisingly, RVG-GNPs-treated mice showed significant reduction in the tumor volume. Significant suppression was shown in the mice treated with RVG-GNP0.01 and RVG-GNP1. The histological images of tissue sections, stained with H&E (FIG. 13), also verified the therapeutic efficacy of RVG-GNPs. Interestingly, substantial tissue deficits were observed at the tissue sections in mice treated with RVG-GNP0.01 and RVG-GNP1. The apoptotic bodies were also observed surrounding to the deficits. It was considered that cellular compounds excreted from necrosized cells might induce immune response nearby the tissues, leading to apoptotic cell death.

As described above, preferable embodiments of the present invention has been exemplified, but the scope of the present invention is not limited to the above particular embodiments, and thus appropriate variations and modifications are possible within the range of claims of the present invention by any person skilled in the art.

The invention claimed is:

1. Gas-generating nanoparticles comprising calcium carbonate crystals and a biocompatible polymer,
   wherein the gas-generating nanoparticles comprise a solid spherical structure formed of the biocompatible polymer,
   the calcium carbonate crystals are distributed within and on the surface of the solid spherical structure, and
   the weight ratio of the calcium carbonate crystals to the biocompatible polymer is 0.001:1 to 1:1.

2. The gas-generating nanoparticles of claim 1, wherein the biocompatible polymer is surface-modified with a rabies virus glycoprotein peptide.

3. The gas-generating nanoparticles of claim 2, wherein the rabies virus glycoprotein peptide includes the amino acid sequence of SEQ ID NO: 1.

4. The gas-generating nanoparticles of claim 1, wherein the biocompatible polymer is a polymer having a structure of polylactide (PLA), polyglycolide (PGA), polylactide-polyglycolide copolymer (PLGA), starch, glycogen, chitin, peptidoglycan, lignosulfonate, tannic acid, lignin, pectin, polyethylene glycol, polyethylene oxide, polyvinyl alcohol, polyethylene oxide-polypropylene oxide block copolymer, cellulose, hemi-cellulose, heparin, hyaluronic acid, dextran, or alginate.

5. The gas-generating nanoparticles of claim 1, wherein the nanoparticles each have a diameter of 100-300 nm.

6. A composition for drug delivery in which a drug is loaded on the gas-generating nanoparticles of claim 1.

7. The composition of claim 6, wherein the drug is a protein, peptide, or nucleotide.

8. A method for preparing gas-generating nanoparticles comprising calcium carbonate crystals and a biocompatible polymer, the method comprising:
   (a) mixing a first water phase containing calcium carbonate crystals with an oil phase containing a biocompatible polymer to form a water-in-oil (w/o) single emulsion;
   (b) mixing the emulsion of step (a) with a second water phase to a water-in-oil-in-water (w/o/w) double emulsion; and
   (c) solidifying the double emulsion of step (b),
   wherein the gas-generating nanoparticles comprise a solid spherical structure formed of the biocompatible polymer,
   the calcium carbonate crystals are distributed within and on the surface of the solid spherical structure, and
   wherein the weight ratio of the calcium carbonate crystals to the biocompatible polymer is 0.001:1 to 1:1.

9. A method for ultrasound imaging, the method comprising administering the gas-generating nanoparticles of claim 1 to a subject, and carrying out ultrasound imaging on the subject.

10. A method for inducing cell necrosis comprising contacting cells with the gas-generating nanoparticles of claim 1 and allowing carbon dioxide to be generated which causes eruption of the cells.

11. The method of claim 10, wherein the cells are administered to a subject.

12. A method for drug delivery, the method comprising administering a composition of claim 6 to a subject.

* * * * *